United States Patent
Pitteloud

Patent Number: 5,925,758
Date of Patent: Jul. 20, 1999

[54] HALS PHOSPHITES AND HALS PHOSPHORAMIDES AS STABILIZERS

[75] Inventor: Rita Pitteloud, Praroman, Switzerland

[73] Assignee: Ciba Specialty Chemicals Corporation, Tarrytown, N.Y.

[21] Appl. No.: 08/416,667

[22] Filed: Apr. 5, 1995

Related U.S. Application Data

[30] Foreign Application Priority Data

Apr. 13, 1994 [CH] Switzerland ............................. 1112/94

[51] Int. Cl.$^6$ .............................. C07F 9/28; C07D 405/00
[52] U.S. Cl. ............................................... 546/25; 546/187
[58] Field of Search ........................ 546/187, 25

[56] References Cited

U.S. PATENT DOCUMENTS

| | | | |
|---|---|---|---|
| 4,096,114 | 6/1978 | Minagawa et al. | 260/45.8 |
| 4,233,412 | 11/1980 | Rody et al. | 525/167 |
| 4,325,863 | 4/1982 | Hinsken et al. | 624/111 |
| 4,338,244 | 7/1982 | Hinsken et al. | 524/109 |
| 5,175,312 | 12/1992 | Dubs et al. | 549/307 |
| 5,216,052 | 6/1993 | Nesvadba et al. | 524/108 |
| 5,239,076 | 8/1993 | Meier et al. | 546/187 |
| 5,252,643 | 10/1993 | Nesvadba et al. | 524/111 |

FOREIGN PATENT DOCUMENTS

| | | |
|---|---|---|
| 356688 | 3/1990 | European Pat. Off. . |
| 5911024 | 4/1994 | European Pat. Off. . |
| 589839 | 9/1994 | European Pat. Off. . |
| 2380290 | 9/1978 | France . |
| 3928291 | 2/1991 | Germany . |
| 4306747 | 9/1993 | Germany . |
| 4316611 | 11/1993 | Germany . |
| 4316622 | 11/1993 | Germany . |
| 4316876 | 11/1993 | Germany . |
| 2247241 | 2/1992 | United Kingdom . |

OTHER PUBLICATIONS

Chemical Abstract 91:21833+ of FR 2,380,290 (1979).
R. Gachter et al. (Ed) Plastics Additives Handbook 3rd Ed. p. 47 (1990).
T. Konig et al. J Prakt chem. 334 (1992) pp. 333–349.
Chem. Abst. 91–21833+ (1979) of FR 2,380,290.
Derw. Abst. 91–066407 of DE 3,928,291 Feb. 1991.
R. Bartlett et al. J. Am. Chem. Soac. 1987, 109 5699–5703.
Derw. Abst. 93–371074 of DE 4,316,611 Nov. 1993.
Derw. Abst — 93–371073 of Germany 4,316,622 Nov. 1993.
Derw. Abst. — 93–353775 of Germany 4,316,876 Nov. 1993.
Derw. Abst. — 94–103409 of EP 589,839 Sep. 1994.
Ullmanns Enzyklopadie der technischen chemie, 3d, 13, Leiten 85–94 (verlag Chemie Weinheim, 1977).

*Primary Examiner*—C. Warren Ivy
*Assistant Examiner*—Raymond Covington
*Attorney, Agent, or Firm*—Luther A. R. Hall; Michele A. Kovaleski

[57] ABSTRACT

The invention relates to novel compounds of the formula I

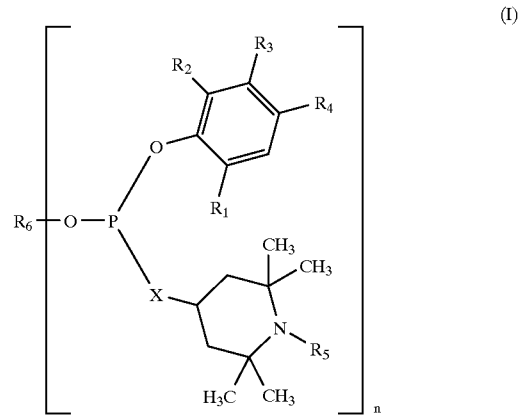

in which the general symbols are as defined in claim 1, as stabilizers for organic materials against oxidative, thermal or light-induced degradation.

16 Claims, No Drawings

HALS PHOSPHITES AND HALS PHOSPHORAMIDES AS STABILIZERS

The present invention relates to novel HALS phosphites and HALS phosphoramides, to compositions comprising an organic material, preferably a polymer, and the novel HALS phosphites and HALS phosphoramides, and to the use thereof for the stabilization of organic materials against oxidative, thermal or light-induced degradation.

Organic phosphites are known in industry as costabilizers, secondary antioxidants and processing stabilizers, in particular for polyolefins; examples of such known phosphite stabilizers are given in R. Gächter/H. Müller (Eds.), Plastics Additives Handbook, 3rd Ed., p. 47, Hanser, Munich, 1990, and EP-A-356 688.

Hindered amines, including, in particular, compounds containing 2,2,6,6-tetramethylpiperidyl groups, are preferably used as light stabilizers (hindered amine light stabilizers, HALS).

Phosphites containing HALS structural units are described, for example, by T. König et al, J. prakt. Chem. 334, 333–349 (1992), in U.S. Pat. No. 5,239,076, GB-A-2 247 241, DE-A-4 306 747 and FR-A-2 380 290.

There continues to be a demand for effective stabilizers for organic materials which are sensitive to oxidative, thermal and/or light-induced degradation.

It has now been found that a selected group of such HALS phosphites and HALS phosphoramides is particularly suitable as stabilizers for organic materials which are sensitive to oxidative, thermal or light-induced degradation. Particular emphasis should be made of the suitability of said compounds as processing stabilizers for synthetic polymers.

The present invention therefore relates to compounds of the formula I

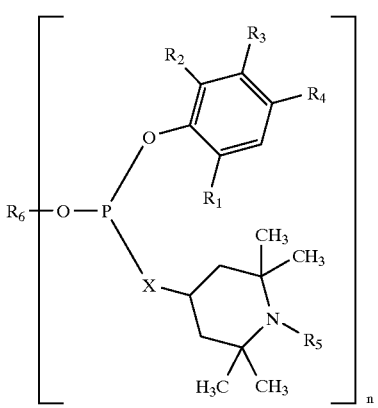

(I)

in which $R_1$ and $R_2$, independently of one another, are hydrogen, $C_1$–$C_{25}$alkyl, $C_2$–$C_{24}$alkenyl, unsubstituted or $C_1$–$C_4$alkyl-substituted $C_5$–$C_8$cycloalkyl; unsubstituted or $C_1$–$C_4$alkyl-substituted phenyl; unsubstituted or $C_1$–$C_4$alkyl-substituted $C_5$–$C_8$cycloalkenyl; $C_7$–$C_9$phenylalkyl or —$CH_2$—S—$R_7$, $R_3$ is hydrogen or methyl, $R_4$ is hydrogen, $C_1$–$C_{25}$alkyl, $C_2$–$C_{24}$alkenyl, unsubstituted or $C_1$–$C_4$alkyl-substituted $C_5$–$C_8$cycloalkyl; unsubstituted or $C_1$–$C_4$alkyl-substituted phenyl; unsubstituted or $C_1$–$C_4$alkyl-substituted $C_5$–$C_8$cycloalkenyl; $C_7$–$C_9$phenylalkyl, —$CH_2$—S—$R_7$, —$(CH_2)_p COOR_8$ or —$(CH_2)_q OR_9$, $R_5$ is hydrogen, $C_1$–$C_8$alkyl, O˙, OH, NO, —$CH_2$CN, $C_1$–$C_{18}$alkoxy, $C_5$–$C_{12}$cycloalkoxy, $C_3$–$C_6$alkenyl, $C_3$–$C_6$alkynyl, $C_1$–$C_8$acyl, or $C_7$–$C_9$phenylalkyl which is unsubstituted or substituted on the phenyl ring by $C_1$–$C_4$alkyl; or $R_5$ furthermore is a radical of the formula II

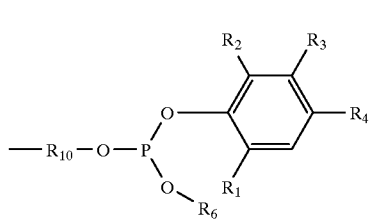

(II)

in which $R_6$ is as defined below for n=1, if n is 1, $R_6$ is $C_1$–$C_{25}$alkyl, $C_2$–$C_{25}$alkyl which is interrupted by oxygen, sulfur or

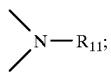

$C_3$–$C_{24}$alkenyl, unsubstituted or $C_1$–$C_4$alkyl-substituted $C_5$–$C_{12}$cycloalkyl; unsubstituted or $C_1$–$C_4$alkyl-substituted $C_5$–$C_{12}$cycloalkenyl; or $C_7$–$C_9$phenylalkyl which is unsubstituted or substituted on the phenyl ring by $C_1$–$C_4$alkyl;

if n is 2, $R_6$ is $C_1$–$C_{25}$alkylene, $C_4$–$C_{25}$alkylene which is interrupted by oxygen, sulfur or

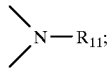

$C_4$–$C_{18}$alkenylene, phenylethylene,

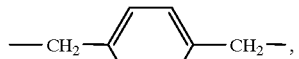

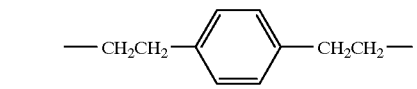

or $C_6$–$C_8$cycloalkylene; or $R_6$ furthermore is a radical of the formula III, IV or V

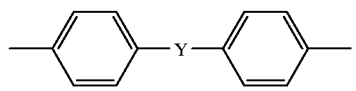

(III)

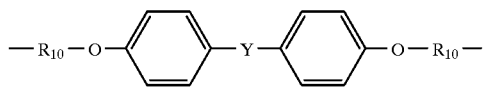

(IV)

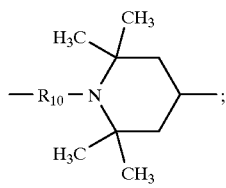

R₇ is C₁–C₁₈alkyl, unsubstituted or C₁–C₄alkyl-substituted C₅–C₁₂cycloalkyl; unsubstituted or C₁–C₄alkyl-substituted phenyl; C₇–C₉phenylalkyl or —(CH₂)ᵣCOOR₈, R₈ is C₁–C₁₈alkyl, unsubstituted or C₁–C₄alkyl-substituted C₅–C₁₂cycloalkyl; unsubstituted or C₁–C₄alkyl-substituted phenyl; or C₇–C₉phenylalkyl;

R₉ is C₁–C₂₅alkyl, unsubstituted or C₁–C₄alkyl-substituted phenyl; C₇–C₉phenylalkyl, C₁–C₂₅alkanoyl, C₃–C₂₅alkenoyl, C₂–C₂₅alkanoyl which is interrupted by oxygen, sulfur or

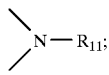

C₆–C₉cycloalkylcarbonyl, unsubstituted or C₁–C₁₂alkyl-substituted benzoyl; thienoyl or furoyl, R₁₀ is C₁–C₁₈alkylene, C₄–C₁₈alkylene which is interrupted by oxygen, sulfur or

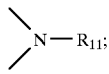

C₄–C₈alkenylene, phenylethylene,

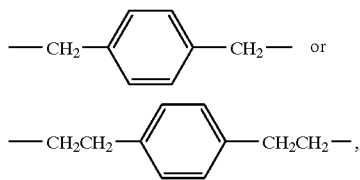

R₁₁ is hydrogen or C₁–C₈alkyl,

R₁₂ and R₁₃, independently of one another, are hydrogen, CF₃, C₁–C₁₂alkyl or phenyl, or R₁₂ and R₁₃, together with the carbon atom to which they are bonded, form an unsubstituted or C₁–C₄alkyl-substituted C₅–C₈cycloalkylidene ring;

R₁₄ is hydrogen, C₁–C₈alkyl or a radical of the formula VI

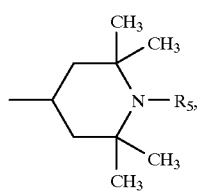

(VI)

X is oxygen or

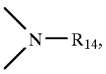

Y is a direct bond, oxygen, sulfur or

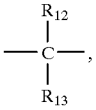

n is 1 or 2,
p is 0, 1 or 2,
q is an integer from 3 to 8, and
r is 1 or 2.

Alkyl having up to 25 carbon atoms is a branched or unbranched radical, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl or docosyl. One of the preferred meanings of R₁, R₂ and R₄ is, for example, C₁–C₁₈alkyl, in particular C₁–C₁₂alkyl, for example C₁–C₈alkyl. Particularly preferred meanings of R₁ and R₂ are methyl and tert-butyl. A particularly preferred meaning of R₄ is tert-butyl.

Alkenyl having 2 to 24 carbon atoms is a branched or unbranched radical, for example vinyl, propenyl, 2-butenyl, 3-butenyl, isobutenyl, n-2,4-pentadienyl, 3-methyl-2-butenyl, n-2-octenyl, n-2-dodecenyl, isododecenyl, oleyl, n-2-octadecenyl or n-4-octadecenyl. Preference is given to alkenyl having 3 to 18, in particular 3 to 12, carbon atoms.

Unsubstituted or C₁–C₄alkyl-substituted C₅–C₁₂cycloalkyl, in particular C₅–C₈cycloalkyl, which preferably contains 1 to 3, in particular 1 or 2, branched or unbranched alkyl radicals, is, for example, cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl, cyclooctyl or cyclododecyl. Preference is given to C₅–C₈cycloalkyl, in particular cyclohexyl.

C₁–C₄alkyl-substituted phenyl, which preferably contains 1 to 3, in particular 1 or 2, alkyl groups, is, for example, o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl or 2,6-diethylphenyl.

Unsubstituted or C₁–C₄alkyl-substituted C₅–C₁₂cycloalkenyl, in particular C₅–C₈cycloalkenyl, which preferably contains 1 to 3, in particular 1 or 2, branched or unbranched alkyl radicals, is, for example, cyclopentenyl, methylcyclopentenyl, dimethylcyclopentenyl, cyclohexenyl, methylcyclohexenyl, dimethylcyclohexenyl, trim ethylcyclohexenyl, tert-butylcyclohexenyl, cycloheptenyl or cyclooctenyl. Preference is given to cyclohexenyl.

C₇–C₉phenylalkyl which is unsubstituted or substituted on the phenyl radical by C₁–C₄alkyl and which preferably contains 1 to 3, in particular 1 or 2, branched or unbranched alkyl radicals is, for example, benzyl, α-methylbenzyl, α,α-dimethylbenzyl, 2-phenylethyl, 2-methylbenzyl, 3-methylbenzyl, 4-methylbenzyl, 2,4-dimethylbenzyl, 2,6-dimethylbenzyl or 4-tert-butylbenzyl. Benzyl is preferred.

Alkoxy having up to 18 carbon atoms is a branched or unbranched radical, for example methoxy, ethoxy, propoxy, isopropoxy, n-butoxy, isobutoxy, pentoxy, isopentoxy, hexoxy, heptoxy, octoxy, decyloxy, tetradecyloxy, hexadecyloxy or octadecyloxy. Preference is given to alkoxy having 6 to 12 carbon atoms.

Cycloalkoxy having 5 to 12 carbon atoms is, for example, cyclopentoxy, cyclohexoxy, cycloheptoxy, cyclooctoxy, cyclodecyloxy or cyclododecyloxy. One of the preferred meanings of $R_5$ is $C_5$–$C_8$cycloalkoxy. Particular preference is given to cyclopentoxy and cyclohexoxy.

Alkynyl having 3 to 6 carbon atoms is a branched or unbranched radical, for example propynyl (propargyl, —CH$_2$—C≡CH ), 2-butynyl or 3-butynyl.

Acyl having 1 to 8 carbon atoms is, for example, formyl, acetyl, propionyl, butyryl, pentanoyl, hexanoyl, heptanoyl, octanoyl, benzoyl, acryloyl or crotonyl. Preference is given to $C_1$–$C_8$alkanoyl, $C_3$–$C_8$alkenoyl or benzoyl, in particular acetyl.

$C_2$–$C_{25}$alkyl which is interrupted by oxygen, sulfur or

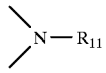

can be interrupted once or more than once and is, for example, CH$_3$—O—CH$_2$—, CH$_3$—S—CH$_2$—, CH$_3$—NH—CH$_2$—, CH$_3$—N(CH$_3$)—CH$_2$—, CH$_3$CH$_2$—N(CH$_3$)—CH$_2$CH$_2$—, CH$_3$—O—CH$_2$CH$_2$—O—CH$_2$CH$_2$—, CH$_3$—(O—CH$_2$CH$_2$—)$_2$O—CH$_2$CH$_2$—, CH$_3$—(O—CH$_2$CH$_2$—)$_3$O—CH$_2$CH$_2$— or CH$_3$—(O—CH$_2$CH$_2$—)$_4$O—CH$_2$CH$_2$—.

$C_1$–$C_{25}$alkylene is a branched or unbranched radical, for example methylene, ethylene, propylene, tetramethylene, pentamethylene, hexamethylene, heptamethylene, octamethylene, decamethylene, dodecamethylene or octadecamethylene. Preference is given to $C_1$–$C_{18}$alkylene, in particular $C_1$–$C_{12}$alkylene, for example $C_1$–$C_8$allylene. A preferred meaning of $R_6$ and $R_{10}$ is ethylene and propylene.

$C_4$–$C_{25}$alkylene, in particular $C_4$–$C_{18}$alkylene, which is interrupted by oxygen, sulfur or

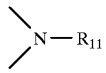

can be interrupted once or more than once and is, for example, —CH$_2$CH$_2$—O—CH$_2$CH$_2$—, —CH$_2$CH$_2$—S—CH$_2$CH$_2$—, —CH$_2$CH$_2$—NH—CH$_2$CH$_2$—, —CH$_2$CH$_2$—N(CH$_3$)—CH$_2$CH$_2$—, —CH$_2$CH$_2$—O—CH$_2$CH$_2$—O—CH$_2$CH$_2$—, —CH$_2$CH$_2$—(O—CH$_2$CH$_2$—)$_2$O—CH$_2$CH$_2$—, —CH$_2$CH$_2$—(O—CH$_2$CH$_2$—)$_3$O—CH$_2$CH$_2$—, —CH$_2$CH$_2$—(O—CH$_2$CH$_2$—)$_4$O—CH$_2$CH$_2$— or —CH$_2$CH$_2$—S—CH$_2$CH$_2$—.

$C_4$–$C_8$alkenylene $R_{10}$ is, for example, 2-buten-1,4-ylene. Phenylethylene is —CH(C$_6$H$_5$)CH$_2$—.

$C_6$–$C_8$cycloalkylene having 6 to 8 carbon atoms is, for example, 1,4-cyclohexylene, 1,3-cyclohexylene, 1,2-cyclohexylene, 1,4-cycloheptylene, 1,3-cycloheptylene, 1,2-cycloheptylene, 1,5-cyclooctylene, 1,4-cyclooctylene, 1,3-cyclooctylene or 1,2-cyclooctylene.

Preference is given to 1,4-cyclohexylene and 1,2-cyclohexylene.

Alkanoyl having up to 25 carbon atoms is a branched or unbranched radical, for example formyl, acetyl, propionyl, butanoyl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, eicosanoyl or docosanoyl. Preference is given to alkanoyl having 2 to 18, in particular 2 to 12, for example 2 to 6, carbon atoms.

Alkenoyl having 3 to 25 carbon atoms is a branched or unbranched radical, for example propenoyl, 2-butenoyl, 3-butenoyl, isobutenoyl, n-2,4-pentadienoyl, 3-methyl-2-butenoyl, n-2-octenoyl, n-2-dodecenoyl, isododecenoyl, oleoyl, n-2-octadecenoyl or n-4-octadecenoyl. Preference is given to alkenoyl having 3 to 18, in particular 2 to 12, for example 2 to 6, carbon atoms.

$C_2$–$C_{25}$alkanoyl, in particular $C_3$–$C_{25}$alkanoyl, which is interrupted by oxygen, sulfur or

can be interrupted once or more than once and is, for example, CH$_3$OCO—, CH$_3$—O—CH$_2$CO—, CH$_3$—S—CH$_2$CO—, CH$_3$—NH—CH$_2$CO—, CH$_3$—N(CH$_3$)—CH$_2$CO—, CH$_3$—O—CH$_2$CH$_2$—O—CH$_2$CO—, CH$_3$—(O—CH$_2$CH$_2$—)$_2$O—CH$_2$CO—, CH$_3$—(O—CH$_2$CH$_2$—)$_3$O—CH$_2$CO— or CH$_3$—(O—CH$_2$CH$_2$—)$_4$O—CH$_2$CO—.

$C_6$–$C_9$cycloalkylcarbonyl is, for example, cyclopentylcarbonyl, cyclohexylcarbonyl, cycloheptylcarbonyl or cyclooctylcarbonyl. Cyclohexylcarbonyl is preferred.

$C_1$–$C_{12}$alkyl-substituted benzoyl, which preferably contains 1 to 3, in particular 1 or 2, alkyl groups, is, for example, o-, m- or p-methylbenzoyl, 2,3-dimethylbenzoyl, 2,4-dimethylbenzoyl, 2,5-dimethylbenzoyl, 2,6-dimethylbenzoyl, 3,4-dimethylbenzoyl, 3,5-dimethylbenzoyl, 2-methyl-6-ethylbenzoyl, 4-tert-butylbenzoyl, 2-ethylbenzoyl, 2,4,6-trimethylbenzoyl, 2,6-dimethyl-4-tert-butylbenzoyl or 3,5-di-tert-butylbenzoyl.

Unsubstituted or $C_1$–$C_4$alkyl-substituted $C_5$-$C_8$cycloalkylidene, which preferably contains 1 to 3, in particular 1 or 2, branched or unbranched alkyl radicals, is for example, cyclopentylidene, methylcyclopentylidene, dimethylcyclopentylidene, cyclohexylidene, methylcyclohexylidene, dimethylcyclohexylidene, trimethylcyclohexylidene, tert-butylcyclohexylidene, cycloheptylidene or cyclooctylidene. Preference is given to cyclohexylidene and tert-butylcyclohexylidene.

Preference is given to compounds of the formula I in which $R_1$ and $R_2$, independently of one another, are hydrogen, $C_1$–$C_{18}$alkyl, $C_2$–$C_{18}$alkenyl, $C_5$–$C_8$cycloallyl, unsubstituted or $C_1$–$C_4$alkyl-substituted phenyl; $C_5$–$C_8$cycloalkenyl, $C_7$–$C_9$phenylalkyl or —CH$_2$—S—R$_7$, $R_4$ is hydrogen, $C_1$–$C_{18}$alkyl, $C_2$–$C_{18}$alkenyl, $C_5$–$C_8$cycloalkyl, unsubstituted or $C_1$–$C_4$alkyl-substituted phenyl; $C_5$–$C_8$-cycloalkenyl, $C_7$–$C_9$-phenylalkyl, —CH$_2$—S—R$_7$, —(CH$_2$)$_p$COOR$_8$ or —(CH$_2$)$_q$OR$_9$, $R_5$ is hydrogen, $C_1$–$C_4$alkyl, OH, —CH$_2$CN, $C_4$–$C_{18}$alkoxy, $C_5$–$C_{12}$cycloalkoxy, allyl, propargyl, acetyl or $C_7$–$C_9$phenylalkyl; or $R_5$ furthermore is a radical of the formula II

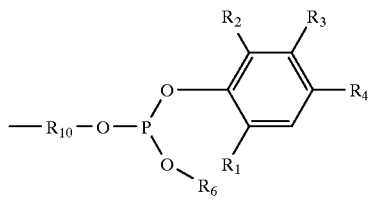
(II)

in which $R_6$ is as defined below for n=1,
if n is 1,
$R_6$ is $C_1$–$C_8$alkyl, $C_3$–$C_{18}$alkyl which is interrupted by oxygen, sulfur or

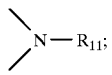

$C_2$–$C_{18}$alkenyl, $C_5$–$C_{12}$cycloalkyl, $C_5$–$C_{12}$cycloalkenyl or $C_7$–$C_9$phenylalkyl which is unsubstituted or substituted on the phenyl ring by $C_1$–$C_4$alkyl;
if n is 2,
$R_6$ is $C_1$–$C_{18}$alkylene, $C_4$–$C_{18}$alkylene which is interrupted by oxygen, sulfur or

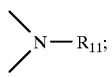

$C_4$–$C_{12}$alkenylene,

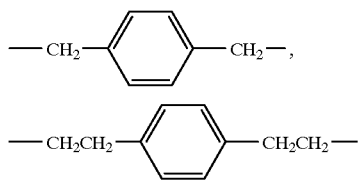

or $C_6$–$C_8$-cycloalkylene; or $R_6$ furthermore is a radical of the formula III or V

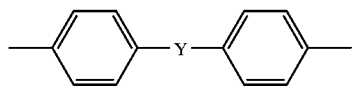 (III)

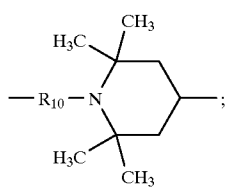 (V)

$R_7$ is $C_1$–$C_{18}$alkyl, $C_5$–$C_{12}$cycloalkyl, unsubstituted or $C_1$–$C_4$alkyl-substituted phenyl; $C_7$–$C_9$phenylalkyl or —(CH$_2$)$_r$COOR$_8$, $R_8$ is $C_1$–$C_{18}$alkyl, $C_5$–$C_{12}$cycloalkyl, unsubstituted or $C_1$–$C_4$alkyl-substituted phenyl; or $C_7$–$C_9$phenylalkyl, $R_9$ is $C_1$–$C_{18}$alkyl, unsubstituted or $C_1$–$C_4$alkyl-substituted phenyl; $C_7$–$C_9$phenylalkyl, $C_1$–$C_{18}$alkanoyl, $C_3$–$C_{18}$alkenoyl, $C_2$–$C_{18}$alkanoyl which is interrupted by oxygen, sulfur or

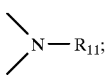

$C_6$–$C_9$cycloalkylcarbonyl, or unsubstituted or $C_1$–$C_4$alkyl-substituted benzoyl, $R_{10}$ is $C_1$–$C_{12}$alkylene, $C_4$–$C_{12}$alkylene which is interrupted by oxygen, sulfur or

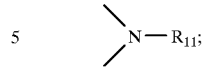

$C_4$–$C_8$alkenylene,

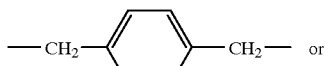 or

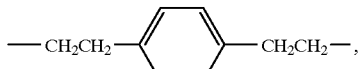

$R_{12}$ and $R_{13}$, independently of one another, are hydrogen, CF$_3$, $C_1$–$C_8$alkyl or phenyl, or $R_{12}$ and $R_{13}$, together with the carbon atom to which they are bonded, form a $C_5$–$C_8$cycloalkylidene ring; and $R_{14}$ is hydrogen or $C_1$–$C_8$alkyl.

Preference is also given to the compounds of the formula I in which $R_1$, $R_2$ and $R_4$, independently of one another, are hydrogen, $C_1$–$C_8$alkyl, cyclohexyl or phenyl.

Preference is likewise given to the compounds of the formula I in which,
if n is 1,
$R_6$ is $C_1$–$C_{12}$alkyl, cyclohexyl or benzyl, and
if n is 2,
$R_6$ is $C_2$–$C_8$alkylene, $C_4$–$C_8$alkylene which is interrupted by

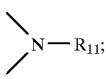

or a radical of the formula III or V

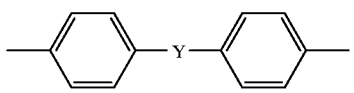 (III)

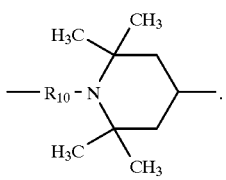 (V)

Particular preference is given to the compounds of formula I in which
$R_1$ and $R_2$, independently of one another, are hydrogen, $C_1$–$C_{12}$alkyl, $C_2$–$C_{12}$alkenyl, cyclohexyl, phenyl, cyclohexenyl or benzyl, $R_4$ is hydrogen, $C_1$–$C_{12}$alkyl, $C_2$–$C_{12}$alkenyl, cyclohexyl, phenyl, cyclohexenyl, benzyl, —CH$_2$—S—$R_7$, —(CH$_2$)$_p$COOR$_8$ or —(CH$_2$)$_q$OR$_9$, $R_5$ is hydrogen, $C_1$–$C_4$alkyl, $C_4$–$C_{16}$alkoxy, $C_5$–$C_8$cycloalkoxy, allyl, propargyl, acetyl or benzyl;

if n is 1, $R_6$ is $C_1$–$C_{12}$alkyl, $C_3$–$C_{12}$alkyl which is interrupted by oxygen or

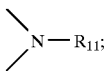

$C_2$–$C_{12}$alkenyl, cyclohexyl, cyclohexenyl or benzyl;

if n is 2, $R_6$ is $C_1$–$C_{12}$alkylene, $C_4$–$C_{12}$alkylene which is interrupted by oxygen or

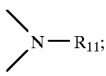

$C_4$–$C_8$alkenylene or cyclohexylene; or $R_6$ furthermore is a radical of the formula III or V

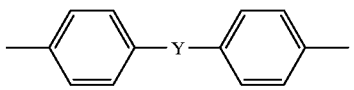
(III)

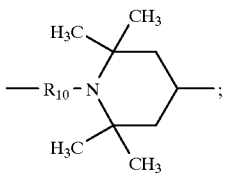
(V)

$R_7$ is $C_1$–$C_{12}$alkyl, $C_5$–$C_8$cycloalkyl, phenyl, benzyl or —(CH$_2$)$_r$COOR$_8$, $R_8$ is $C_1$–$C_{12}$alkyl, $C_5$–$C_8$cycloalkyl, phenyl or benzyl, $R_9$ is $C_1$–$C_{12}$alkyl, phenyl, benzyl, $C_1$–$C_{12}$alkanoyl, $C_2$–$C_{12}$alkanoyl which is interrupted by oxygen; cyclohexylcarbonyl or benzoyl, $R_{10}$ is $C_1$–$C_8$alkylene, $C_4$–$C_8$alkylene which is interrupted by oxygen, or $C_4$–$C_8$alkenylene, $R_{12}$ and $R_{13}$, independently of one another, are hydrogen, CF$_3$ or $C_1$–$C_4$alkyl, or $R_{12}$ and $R_{13}$, together with the carbon atom to which they are bonded, form a cyclohexylidene ring;

Y is a direct bond, oxygen or

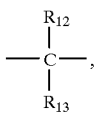

p is 2,
q is an integer from 3 to 6, and
r is 1.

Of particular interest are the compounds of the formula I in which $R_1$ and $R_2$, independently of one another, are hydrogen, $C_1$–$C_8$alkyl, cyclohexyl or phenyl, $R_4$ is hydrogen, $C_1$–$C_8$alkyl, cyclohexyl or —(CH$_2$)$_p$COOR$_8$, $R_5$ is hydrogen, $C_1$–$C_4$alkyl, $C_6$–$C_{12}$alkoxy, acetyl or benzyl;

if n is 1, $R_6$ is $C_1$–$C_{12}$alkyl, cyclohexyl or benzyl;

if n is 2, $R_6$ is $C_2$–$C_8$alkylene, $C_4$–$C_8$alkylene which is interrupted by

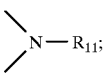

or a radical of the formula III or V

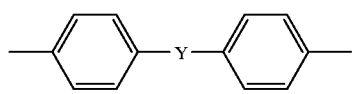
(III)

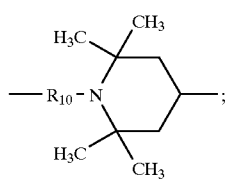
(V)

$R_8$ is $C_1$–$C_{12}$alkyl or benzyl, $R_{10}$ is $C_1$–$C_8$alkylene or $C_4$–$C_8$alkylene which is interrupted by oxygen, $R_{12}$ and $R_{13}$, independently of one another, are hydrogen or $C_1$–$C_4$alkyl, or $R_{12}$ and $R_{13}$, together with the carbon atom to which they are bonded, form a cyclohexylidene ring;

Y is a direct bond or

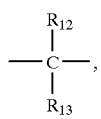

and
p is 2.

Of specific interest are the compounds of the formula I in which $R_1$ and $R_2$, independently of one another, are $C_1$–$C_4$alkyl, $R_3$ is hydrogen, $R_4$ is $C_1$–$C_4$alkyl, $R_5$ is methyl;

if n is 1, $R_6$ is $C_1$–$C_{12}$alkyl or benzyl, if n is 2, $R_6$ is propylene, butylene which is interrupted by

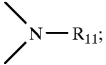

or a radical of the formula V

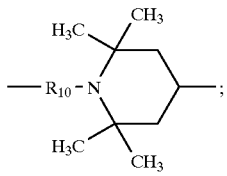
(V)

$R_{10}$ is ethylene, $R_{11}$ is methyl, $R_{14}$ is $C_1$–$C_4$alkyl,

X is oxygen or

and n is 1 or 2.

The novel compounds of the formula I can be prepared in a manner known per se.

For example, and this is preferred, a phosphorodichloridite of the formula VII is reacted with an HALS compound of the formula VIII

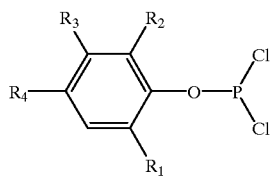
(VII)

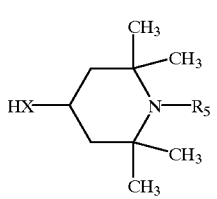
(VIII)

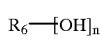
(IX)

in which $R_1$, $R_2$, $R_3$, $R_4$, $R_5$ and X are as defined above, to give an intermediate of the formula X, or a phosphordichloridite of the formula VII is reacted with a compound of the formula IX in which $R_6$ and n are as defined above, to give an intermediate of the formula XI

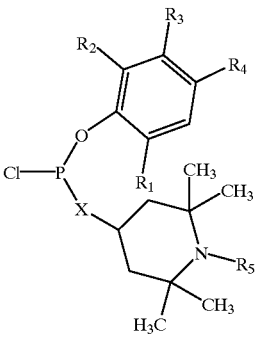
(X)

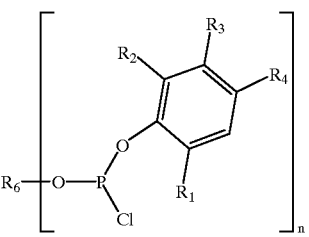
(XI)

The intermediate of the formula X is subsequently reacted with a compound of the formula IX, and the intermediate of the formula XI is reacted with an HALS compound of the formula VIII to give the novel compounds of the formula I.

Preferably, the phosphorodichloridite of the formula VII is first reacted with an HALS compound of the formula VIII.

The intermediates of the formulae X and XI are expediently not isolated and are reacted, without purification, with a compound of the formula IX or an HALS compound of the formula VIII with elimination of hydrochloric acid to give the novel compounds of the formula I.

If n is 1 in the compound of the formula IX, both the phosphorodichloridite of the formula VII and the intermediate of the formula X are preferably employed in equimolar amounts with respect to the compound of the formula IX.

If n is 2 in the compound of the formula IX, two equivalents, with respect to the compound of the formula IX employed, of each of the phosphorodichlordite of the formula VII and of the intermediate of the formula X are preferably used.

In the reaction of the intermediates of the formulae X and XI to give the novel compounds of the formula I, the compound of the formula IX or the HALS compound of the formula VIII is expediently used in a slight excess.

The reaction of the phosphorodichloridite of the formula VII in the presence of a mixture comprising an HALS compound of the formula VIII and the compound of the formula IX likewise gives the novel compounds of the formula I.

The reaction is carried out in the melt or in the presence of a suitable organic, polar or apolar, aprotic solvent. This reaction is preferably carried out in the presence of a base at temperatures between 0° C. and the boiling point of the solvent, in particular at temperatures between 10 and 150° C.

Bases such as amines can simultaneously also be used as solvent.

The base can be employed in various amounts, from catalytic via stochiometric amounts up to an excess of several times the molar amount with respect to the compounds of the formula VII, VIII or IX employed. The hydrogen chloride formed during the reaction is, if appropriate, converted through the base into chloride, which can be removed by filtration and/or washing with a suitable aqueous or solid phase; a second, water-immiscible solvent can also be employed here. The products are expediently isolated by evaporating the organic phase and drying the residue. The products are expediently purified by chromatography on silica gel or by recrystallization.

Suitable solvents for carrying out the reaction include hydrocarbons (for example mesitylene, toluene, xylene, hexane, pentane or other petroleum ether fractions), halogenated hydrocarbons (for example di- or trichloromethane, 1,2-dichloroethane, 1,1,1-trichloroethane or chlorobenzene), ethers (for example diethyl ether, dibutyl ether or tetrahydrofuran), ketones (for example acetone, ethyl methyl ketone, diethyl ketone, methyl propyl ketone or cyclohexanone), furthermore acetonitrile, butyl acetate, dimethyl formamide, dimethyl sulfoxide or N-methylpyrrolidone.

Suitable bases include primary, secondary and in particular tertiary amines (for example trimethylamine, triethylamine, tributylamine, N,N-dimethylaniline, N,N-diethylaniline or pyridine), hydrides (for example lithium hydride, sodium hydride or potassium hydride) or alkoxides (for example sodium methoxide).

If hydrides (for example sodium hydride, sodium borohydride or lithium aluminium hydride), alkali metals, alkali metal hydroxides or sodium methoxide are used as bases, the corresponding alkoxide of the compound of the formula VIII or IX can first be formed; any reaction product formed (for example water or methanol) is removed by distillation (for example as an azeotrope with toluene) before the reaction with the compound of the formula VII.

The compounds of the formula VII are known or can be prepared by processes known per se, as described, for example, in DE-A-3 928 291 or by R. A. Bartlett et al, J. Amer. Chem. Soc. 109 (19), 5699 (1987).

The compounds of the formula VII required for the preparation of the novel compounds of the formula I can be prepared in situ analogously to the abovementioned literature procedures, and reacted further, without isolation, with the compounds of the formulae VIII and IX to give the compounds of the formula I.

The HALS compounds of the formula VIII are known or can be prepared by processes known per se, as described, for example, in U.S. Pat. No. 4,233,412.

The compounds of the formula IX are known or can be prepared by processes known per se.

Compounds of the formula I in which $R_5$ is a radical of the formula II are prepared, for example, by reacting two equivalents of the intermediate of the formula XI with one equivalent of the HALS compound of the formula XII

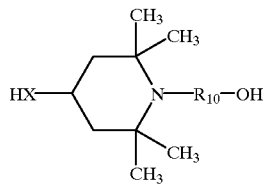

(XII)

in which $R_{10}$ and X are as defined above.

The preferred reaction conditions, for example temperature, solvent, base or catalyst, correspond to those as described above.

The HALS compounds of the formula XII are known or can be prepared by processes known per se, as described, for example, in U.S. Pat. No. 4,233,412.

The novel compounds of the formula I are suitable for the stabilization of organic materials against oxidative, thermal or light-induced degradation.

Examples of such materials are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly($\alpha$-methylstyrene).

6. Copolymers of styrene or a-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or $\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

The invention therefore furthermore relates to compositions comprising (a) an organic material subjected to oxidative, thermal or light-induced degradation and (b) at least one compound of the formula I.

The organic materials to be protected are preferably natural, semisynthetic or preferably synthetic organic materials. Particular preference is given to thermoplastic polymers, in particular PVC or polyolefins, in particular polyethylene and polypropylene.

Particular emphasis should be placed on the action of the novel compounds against thermal and oxidative degradation, in particular on heating, as occurs in the processing of thermoplastics. The novel compounds are therefore highly suitable for use as processing stabilizers.

The compounds of the formula I are preferably added to the material to be stabilized in amounts of from 0.01 to 10%, for example from 0.01 to 5%, preferably from 0.025 to 3%, in particular from 0.025 to 1%, based on the weight of the organic material to be stabilized.

In addition to the compounds of the formula I, the novel compositions can contain further costabilizers, for example the following:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethyliphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis-(2,6-dimethyl-4-hydroxyphenyl) disulfide.

1.6. Alkylidenebisphenols, for example 2,2'-methylenebis (6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl) dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tris-(3,5-di-tert-butyl-4-hydroxybenzyl)amine, bis(4-tert-butyl-3'-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis-[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis (octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris (3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) pronionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamine, N,N'-bis (3,5-di-tert-butyl-4-hydroxyphenylpropionyl) trimethylenediamine, N,N'-bis(3,5-di-tert-butyl-4-hydroxyphenylpropionyl)hydrazine.

2. UV absorbers and light stabilisers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl) benzotriazole, 2-(2'-hydroxy-4'-octyloxyphenyl) benzotriazole, 2-(3',5'-di-tert-amyl-2'-hydroxyphenyl) benzotriazole, 2-(3',5'-bis-(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3-tert-butyl-2'-hydroxy-5'-(2-methoxycarbonylethyl) phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole, and 2-(3-tert-butyl-2'hydroxy-5'-(2-isooctyloxycarbonylethyl) phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—$CH_2CH_2$—COO$(CH_2)_3$]$_2$, where R=3'-tert-butyl-4'-hydroxy-5'-2H-benzotriazol-2-ylphenyl.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis (4-tert-butylbenzoyl) resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-piperidyl)sebacate, bis(2,2,6,6-tetramethyl-piperidyl)succinate, bis(1,2,2,6,6-pentamethylpiperidyl) sebacate, bis(1,2,2,6,6-pentamethylpiperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazasprio[4.5]decan-2,4-dion, bis(1-octyloxy-2,2,6,6-tetramethylpiperidyl) sebacate, bis(1-octyloxy-2,2,6,6-tetramethylpiperidyl) succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis (4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl- 1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl) pyrrolidine-2,5-dione.

2.7. Oxamides, for example 4,4'-dioctyloxyoxanilide, 2,2'-diethoxyoxanllide, 2,2'-dioctyloxy-5,5'-di-tertbutoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and para-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythiritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphsophite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl- 12-methyl-dibenz[d,g]-1,3,2-dioxaphosphocin, bis(2,4-di-tert-butyl-6-methylphenyl) methylphosphite, bis(2,4-di-tert-butyl-6-methylphenyl) ethylphosphite.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

8. Nucleating agents, for example, 4-tert-butylbenzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxides, carbon black, graphite.

10. Other additives, for example, plasticisers, lubricants, emulsifiers, pigments, optical brighteners, flameproofing agents, antistatic agents and blowing agents.

11. Benzofuranones and indolinones, for example those disclosed in U.S. Pat. Nos. 4,325,863, 4,338,244, 5,175,312, 5,216,052, 5,252,643, DE-A-4 316 611, DE-A-4 316 622, DE-A-4 316 876, EP-A-0 589 839 or EP-A-0 591 102 or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]-phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one.

The costabilizers, with the exception of the benzofuranones mentioned under point 11, are added, for example, in concentrations of from 0.01 to 10%, based on the total weight of the material to be stabilized.

Other preferred compositions comprise, in addition to component (a) and the compounds of the formula I, other additives, in particular phenolic antioxidants, light stabilizers and/or processing stabilizers.

Particularly preferred additives are phenolic antioxidants (point 1 in the list), sterically hindered amines (point 2.6 in the list), phosphites and phosphonites (point 4 in the list) and peroxide scavengers (point 5 in the list).

Other additives (stabilizers) which are likewise particularly preferred are benzofuran-2-ones, as described, for example, in U.S. Pat. Nos. 4,325,863, 4,338,244, 5,175,312, 5,216,052, 5,252,643, DE-A-4 316 611, DE-A-4 316 622, DE-A-4 316 876, EP-A-0 589 839 and EP-A-0 591 102.

Examples of such benzofuran-2-ones are compounds of the formula

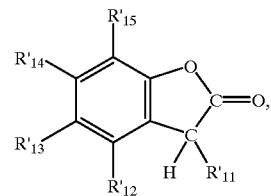

in which $R'_{11}$ is an unsubstituted or substituted carbocyclic or heterocyclic aromatic ring system, $R'_{12}$ is hydrogen;

$R'_{14}$ is hydrogen, alkyl having 1 to 12 carbon atoms, cyclopentyl, cyclohexyl or chlorine;

$R'_{13}$ is as defined for $R'_{12}$ or $R'_{14}$ or is a radical of the formula

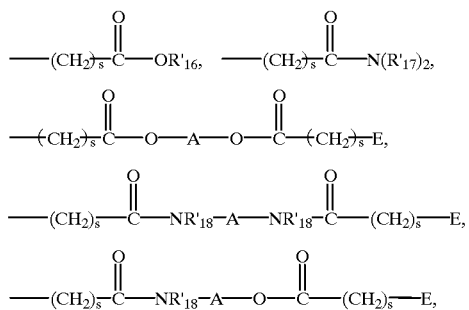

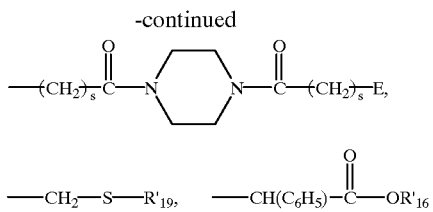

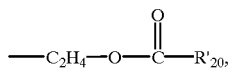

or -D-E, in which

R'$_{16}$ is hydrogen, alkyl having 1 to 18 carbon atoms, alkyl having 2 to 18 carbon atoms which is interrupted by oxygen or sulfur, dialkylaminoalkyl having a total of 3 to 16 carbon atoms, cyclopentyl, cyclohexyl, phenyl or phenyl which is substituted by 1 to 3 alkyl radicals having a total of at most 18 carbon atoms;

s is 0, 1 or 2;

the substituents R'$_{17}$, independently of one another, are hydrogen, alkyl having 1 to 18 carbon atoms, cyclopentyl, cyclohexyl, phenyl, phenyl which is substituted by 1 or 2 alkyl radicals having a total of at most 16 carbon atoms, a radical of the formula —C$_2$H$_4$OH, —C$_2$H$_4$—O—C$_t$H$_{2t+1}$ or

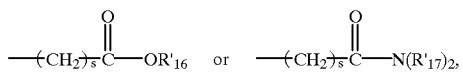

or, together with the nitrogen atom to which they are bonded, form a piperidine or morpholine radical;

t is from 1 to 18;

R'$_{20}$ is hydrogen, alkyl having 1 to 22 carbon atoms or cycloalkyl having 5 to 12 carbon atoms;

A is alkylene having 2 to 22 carbon atoms which may be interrupted by nitrogen, oxygen or sulfur;

R'$_{18}$ is hydrogen, alkyl having 1 to 18 carbon atoms, cyclopentyl, cyclohexyl, phenyl, phenyl which is substituted by 1 or 2 alkyl radicals having a total of at most 16 carbon atoms, or benzyl;

R'$_{19}$ is alkyl having 1 to 18 carbon atoms;

D is —O—, —S—, —SO—, —SO$_2$— or —C(R'$_{21}$)$_2$—;

the substituents R'$_{21}$, independently of one another, are hydrogen, C$_1$–C$_{16}$alkyl, where the two R'$_{21}$ radicals together contain 1 to 16 carbon atoms, R'$_{21}$ is furthermore phenyl or a radical of the formula

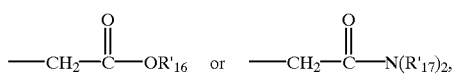

in which s, R'$_{16}$ and R'$_{17}$ are as defined above;

E is a radical of the formula in which R'$_{11}$, R'$_{12}$ and R'$_{14}$ are as defined above; and R'$_{15}$ is hydrogen, alkyl having 1 to 20 carbon atoms, cyclopentyl, cyclohexyl, chlorine or a radical of the formula

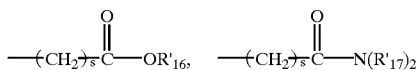

in which R'$_{16}$ and R'$_{17}$ are as defined above, or R'$_{15}$ together with R'$_{14}$ forms a tetramethylene radical.

Preference is given to benzoforan-2-ones in which R'$_{13}$ is hydrogen, alkyl having 1 to 12 carbon atoms, cyclopentyl, cyclohexyl, chlorine or a radical of the formula

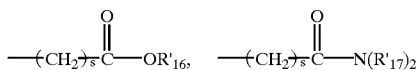

or -D-E, in which s, R'$_{16}$, R'$_{17}$, D and E are as defined above, and R'$_{16}$ is, in particular, hydrogen, alkyl having 1 to 18 carbon atoms, cyclopentyl or cyclohexyl.

Preference is also given to benzofuran-2-ones in which R'$_{11}$ is phenyl or phenyl which is substituted by 1 or 2 alkyl radicals having a total of at most 12 carbon atoms; R'$_{12}$ is hydrogen; R'$_{14}$ is hydrogen or alkyl having 1 to 12 carbon atoms; R'$_{13}$ is hydrogen, alkyl having 1 to 12 carbon atoms,

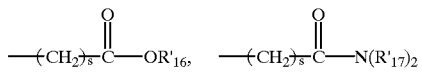

or -D-E;

R'$_{15}$ is hydrogen, alkyl having 1 to 20 carbon atoms,

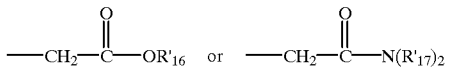

or R'$_{15}$ together with R'$_{14}$ forms a tetramethylene radical, where s, R'$_{16}$, R'$_{17}$, D and E are as defined at the outset.

Likewise of particular interest are benzofuran-2-ones in which R'$_{13}$ is hydrogen, alkyl having 1 to 12 carbon atoms or -D-E; R'$_{12}$ and R'$_{14}$, independently of one another, are hydrogen or alkyl having 1 to 4 carbon atoms; and R'$_{15}$ is alkyl having 1 to 20 carbon atoms, where D and E are as defined at the outset.

Finally, likewise of particular interest are benzofuran-2-ones in which R'$_{13}$ is alkyl having 1 to 4 carbon atoms or -D-E; R'$_{12}$ and R'$_{14}$ are hydrogen; and R'$_{15}$ is alkyl having 1 to 4 carbon atoms, cyclopentyl or cyclohexyl, where D is a —C(R'$_{21}$)$_2$— group and E is a radical of the formula

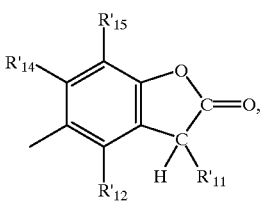

where the substituents R'$_{21}$ are identical or different and are each alkyl having 1 to 4 carbon atoms, and R'$_1$l, R'$_{12}$, R'$_{14}$ and R'$_{15}$ are as defined above.

The amount of benzofuran-2-ones additionally employed can vary within broad limits. For example, they can be present in the novel compositions in amounts of from 0.0001 to 5% by weight, preferably from 0.001 to 2% by weight, in particular from 0.01 to 2% by weight.

The compounds of the formula I and any further additives are incorporated into the polymeric, organic material by known methods, for example before or during shaping or alternatively by application of the dissolved or dispersed compounds to the polymeric, organic material, if necessary with subsequent evaporation of the solvent. The novel compounds of the formula I can also be added to the materials to be stabilized in the form of a masterbatch, which contains these in, for example, a concentration from 2.5 to 25% by weight.

The novel compounds of the formula I can also be added before or during polymerization or before crosslinking.

The compounds of the formula I can be incorporated into the material to be stabilized in pure form or in encapsulated in waxes, oils or polymers.

The compounds of the formula I can also be sprayed onto the polymer to be stabilized. They are capable of diluting other additives (for example the conventional additives mentioned above) or their melts, so that they can also be sprayed onto the polymer to be stabilized together with these additives. A particularly advantageous method is the addition by spraying during deactivation of the polymerization catalysts, where, for example, the steam used for deactivation can be used for the spraying.

In the case of polyolefins polymerized in bead form, it may, for example, be advantageous to apply the novel compounds of the formula I, if desired together with other additives, by spraying.

The materials stabilized in this way can be used in a very wide variety of forms, for example as films, fibres, tapes, moulding compositions, profiles or as binders for paints, adhesives or adhesive cements.

As mentioned above, the organic materials to be protected are preferably organic polymers, particularly synthetic polymers. Thermoplastic materials, in particular polyolefins, are particularly advantageously protected. In particular, the excellent activity of the compounds of the formula I as processing stabilizers (heat stabilizers) should be emphasized. For this purpose, they are advantageously added to the polymer before or during processing thereof. However, other polymers (for example elastomers) or lubricants or hydraulic fluids can also be stabilized against degradation, for example light-induced or thermo-oxidative degradation. Elastomers are given in the above list of possible organic materials.

Suitable lubricants and hydraulic fluids are based, for example, on mineral or synthetic oils or mixtures thereof. The lubricants are known to the person skilled in the art and are described in the relevant specialist literature, for example in Dieter Klamann "Schmierstoffe und verwandte Produkte" [Lubricants and Related Products] (Verlag Chemie, Weinheim, 1982), in Schewe-Kobek, "Das Schmiermittel-Taschenbuch" [The Lubricant Handbook] (Dr. Alfred H üithig-Verlag, Heidelberg, 1974) and in "Ullmanns Enzyklopädie der technischen Chemie" [Ullmann's Encyclopedia of Industrial Chemistry], Vol. 13, pages 85–94 (Verlag Chemie, Weinheim, 1977).

A preferred embodiment of the present invention is therefore the use of compounds of the formula I for the stabilization of organic materials against oxidative, thermal or light-induced degradation.

The novel compounds of the formula I are distinguished by pronounced excellent hydrolysis stability and advantageous colouring behaviour, ie low discoloration of the organic materials during processing.

Organic materials which have been stabilized by means of the compounds of the present invention are particularly well protected against light-induced degradation.

The present invention therefore also relates to a process for the stabilization of an organic material against oxidative, thermal or light-induced degradation, which comprises incorporating or applying at least one compound of the formula I into or to this material.

The examples below illustrate the invention in greater detail. Parts and percentages are by weight.

EXAMPLE 1

Preparation of the Compound (101) (Table 1)

A solution of 4.28 g (25.0 mmol) of 1,2,2,6,6-pentamethylpiperidin-4-ol in 50 ml of toluene is added dropwise at 10° C. to a stirred solution, under a nitrogen atmosphere, of 8.03 g (25.0 mmol) of 2,4-di-tert-butyl-6-methylphenylphosphorodichloridite and 4.18 ml (30.0 mmol) of triethylamine in 50 ml of toluene. The suspension is stirred at 10° C. for 15 minutes. 4.18 ml (30.0 mmol) of triethylamine are subsequently added, and the solution of 4.66 g (25.0 mmol) of n-dodecanol in 50 ml of toluene is then added dropwise. The reaction mixture is stirred at room temperature for 3 hours. The white suspension is filtered through Celite, and the filtrate is evaporated on a vacuum rotary evaporator. Chromatography of the residue on silica gel using the eluate system hexane/ethyl acetate 19:1 to 9:1 gives 11.4 g (75%) of the compound (101) as a colourless oil (Table 1).

EXAMPLE 2

Preparation of the Compound (102) (Table 1).

A solution of 5.14 g (30.0 mmol) of 1,2,2,6,6-pentamethylpiperidin-4-ol in 60 ml of toluene is added dropwise at 10° C. to a stirred solution, under a nitrogen atmosphere, of 9.64 g (30.0 mmol) of 2,4-di-tert-butyl-6-methylphenylphosphorodichlorite and 3.64 ml (36.0 mmol) of triethylamine in 40 ml of toluene. The white suspension is stirred at 10° C. for 15 minutes. 3.64 g (36.0 mmol) of triethylamine are subsequently added, and a solution of 1.14 g (15.0 mmol) of 1,3-propanediol in 10 ml of toluene is then added dropwise.

The white suspension is stirred at 60° C. for 4 hours, then cooled to room temperature and filtered through Celite, and the filtrate is evaporated on a vacuum rotary evaporator. Chromatography of the residue on silica gel using the eluate system hexane/ethyl acetate 3:1 to 1:1 gives 8.4 g (61%) of compound (102) as a highly viscous oil (Table 1).

Replacement of 1,3-propanediol in Example 2 by N-methyldiethanolamine or N-2'-hydroxyethyl-4-hydroxy-2,2,6,6,-tetramethylpiperidine gives compound (103) (yield 52%) or (105) yield 88%) (Table 1).

Replacement of 2,4-di-tert-butyl-6-methyl-phenylphosphorodichloridite in Example 2 by 2,6-di-tert-butyl-4-methylphenylphosphorodichloridite gives compound (104) (yield 77%) (Table 1).

EXAMPLE 3

Preparation of Compound (106) (Table 1).

A solution of 9.06 g (40.0 mmol) 4-n-butylamino-1,2,2,6,6-pentamethylpiperidine in 20 ml of toluene is added dropwise at 10° C. to a stirred solution, under a nitrogen atmosphere, of 12.85 g (40.0 mmol) of 2,4-di-tert-butyl-6-methylphenylphosphorodichloridite and 6.70 ml (48.0 mmol) of triethylamine in 180 ml of toluene. The white suspension is stirred at 60° C. for 1 hour. 6.70 ml (48.0 mmol) of triethylamine are subsequently added, and 4.75 ml (3.85 g, 52.0 mmol) of 1-butanol are then added dropwise. The white suspension is stirred at 60° C. for 3 hours, then cooled to room temperature and filtered through Celite, and the filtrate is evaporated on a vacuum rotary evaporator. Chromatography of the residue on silica gel using the eluate system hexane/ethyl acetate 3:1 to 1:1 gives 11.8 g (54%) of compound (106) as a viscous oil (Table 1).

Replacement of 1-butanol in Example 3 by benzyl alcohol gives compound (107) (yield 76%) (Table 1).

TABLE 1

| No. | Compound | m.p. °C. | C (%), H (%), N (%) (calculated/found) | ³¹P-NMR (CDCl₃) (ppm) |
|-----|----------|----------|----------------------------------------|------------------------|
| 101 | (structure: 1,2,2,6,6-pentamethylpiperidin-4-yl 2,4-di-tert-butyl-6-methylphenyl dodecyl phosphite) | Oil | 73.34 11.31 2.31 / 74.27 11.52 2.00 | 140.005 |
| 102 | (structure: bis[(1,2,2,6,6-pentamethylpiperidin-4-yl)(2,4-di-tert-butyl-6-methylphenyl)phosphite] linked by –O–CH₂–CH₂–CH₂–O–) | Oil | 69.55 10.13 3.06 / 69.42 10.22 2.84 | 140.08 |
| 103 | (structure: bis[(1,2,2,6,6-pentamethylpiperidin-4-yl)(2,4-di-tert-butyl-6-methylphenyl)phosphite] linked by –O(CH₂)₂–N(CH₃)–(CH₂)₂–O–) | Oil | 68.93 10.20 4.38 / 69.58 10.39 3.57 | 139.76 |

TABLE 1-continued
| No. | Compound | m.p. °C. | C (%), H (%), N (%) (calculated/found) | $^{31}$P-NMR (CDCl$_3$) (ppm) |
|---|---|---|---|---|
| 104 | 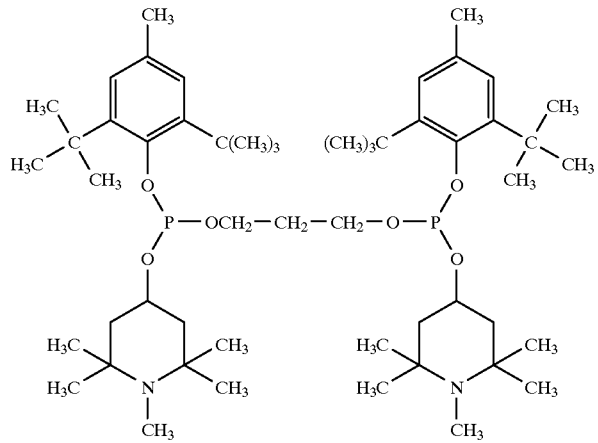 | Oil | 69.55 10.13 3.06<br>69.18 10.25 2.81 | 146.15 |
| 105 | 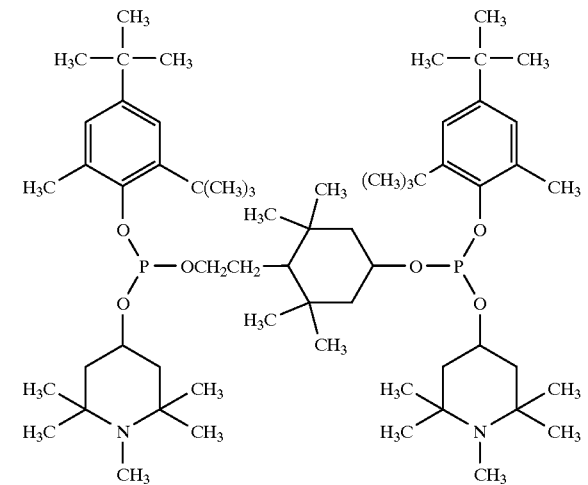 | Oil | 70.42 10.37 4.04<br>70.50 10.32 3.61 | 140.057<br>and<br>140.979 |
| 106 | 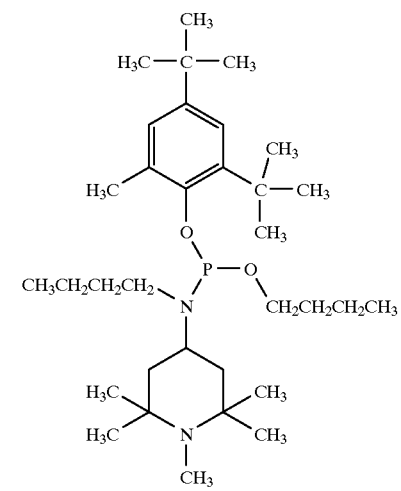 | Oil | 72.22 11.20 5.10<br>72.25 11.33 5.29 | 152.37 |

TABLE 1-continued

| No. | Compound | m.p. °C. | C (%), H (%), N (%) (calculated/found) | $^{31}$P-NMR (CDCl$_3$) (ppm) |
|---|---|---|---|---|
| 107 | (structure shown) | Oil | 74.19 10.20 4.81<br>74.26 10.30 4.63 | 153.31 |

EXAMPLE 4

Stabilization of Polypropylene During Multiple Extrusion.

1.3 kg of polypropylene powder (®Profax 6501) which has been prestabilized by means of 0.025% of Irganox® 1076 (n-octadecyl (3-[3,5-di-tert-butyl-4-hydroxyphenyl] propionate) (having a melt flow index of 3.2, measured at 230° C. and 2.16 kg) are mixed with 0.05% of Irganox® 1010 (pentaerythirityl tetrakis[3-(3,5-di-tert-butyl-4-hydroxyphenyl)propionate]), 0.05% of calcium stearate, 0.03% of dihydrotalcite [DHT 4A®, Kyowa Chemical Industry Co., Ltd., Mg$_{4.5}$Al$_2$(OH)$_{13}$CO$_3$.3.5 H$_2$O] and 0.05% of the compound from Table 1. This mixture is extruded in an extruder having a barrel diameter of 20 mm and a length of 400 mm at 100 revolutions per minute, the three heating zones being set at the following temperatures: 260, 270, 280° C. The extrudate is cooled by drawing through a water bath and subsequently granulated. These granules are re-extruded. After 3 extrusions, the melt flow index is measured (at 230° C. and 2.16 kg). A large increase in the melt flow index means considerable chain degradation, ie poor stabilization. The results are shown in Table 2.

TABLE 2

| Compound from Table 1 | Melt flow index after 3 extrusions |
|---|---|
| — | 20.0 |
| 101 | 4.9 |
| 102 | 5.0 |
| 103 | 5.2 |
| 104 | 4.7 |
| 105 | 4.7 |
| 107 | 4.6 |

Table 3: Stabilization of polyethylene during processing.

100 parts of polyethylene powder (Lupolen®5260 Z) are mixed with 0.05 part of Irganox® 1010 (pentaerythrityl tetrakis[3-(3,5-di-tert-butyl-4-hydroxyphenyl)propionate]) and 0.1 part of stabilizer from Table 1, and the mixture is compounded in a Brabender Plastograph at 220° C. and 50 revolutions per minute. During this time, the compounding resistance is recorded continuously as torque. During the compound time, the polymer, after an extended constant time, begins to cross link, which is evident from the rapid increase in torque. Table 3 shows the time before significant increase in the torque as a measure of the stabilizer action. The longer this time, the better the stabilizer action.

TABLE 3

| Compound from Table 1 | Time before torque increase (min.) |
|---|---|
| — | 5.0 |
| 101 | 14.5 |
| 102 | 13.0 |
| 104 | 12.0 |

What is claimed is:
1. A compound of the formula I

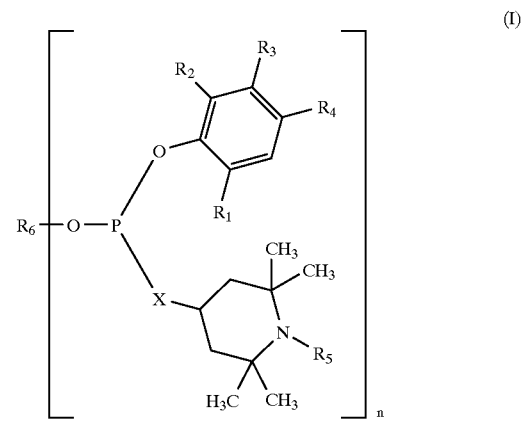

(I)

in which $R_1$ and $R_2$, independently of one another, are hydrogen, $C_1$–$C_{25}$alkyl, $C_2$–$C_{24}$alkenyl, unsubstituted or $C_1$–$C_4$alkyl-substituted $C_5$–$C_8$cycloalkyl; unsubstituted or $C_1$–$C_4$alkyl-substituted phenyl; unsubstituted or $C_1$–$C_4$alkyl-substituted $C_5$–$C_8$cycloalkenyl; $C_7$–$C_9$phenylalkyl or —CH$_2$—S—R$_7$, $R_3$ is hydrogen or methyl, $R_4$ is hydrogen, $C_1$–$C_{25}$alkyl, $C_2$–$C_{24}$alkenyl, unsubstituted or $C_1$–$C_4$alkyl-substituted $C_5$–$C_8$cycloalkyl; unsubstituted or $C_1$–$C_4$alkyl-substituted phenyl; unsubstituted or $C_1$–$C_4$alkyl-substituted $C_5$–$C_8$cycloalkenyl; $C_7$–$C_9$phenylalkyl, —CH$_2$—S—R$_7$, —(CH$_2$)$_p$COOR$_8$ or —(CH$_2$)$_q$OR$_9$, $R_5$ is hydrogen, $C_1$–$C_8$alkyl, O˙, OH, NO, —CH$_2$CN, $C_1$–$C_{18}$alkoxy, $C_5$–$C_{12}$cycloalkoxy, $C_3$–$C_6$alkenyl, $C_3$–$C_6$alkynyl, $C_1$–$C_8$acyl, or $C_7$–$C_9$phenylalkyl which is unsubstituted or substituted on the phenyl ring by $C_1$–$C_4$alkyl; or $R_5$ furthermore is a radical of the formula II

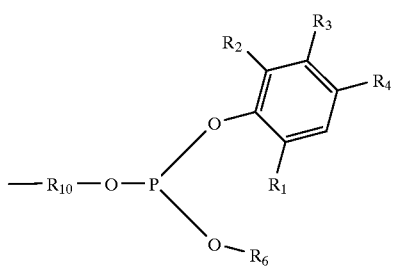

(II)

in which $R_6$ is as defined below for n=1, if n is 1, $R_6$ is $C_1$–$C_{25}$alkyl, $C_2$–$C_{25}$alkyl which is interrupted by oxygen, sulfur or

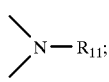

$C_3$–$C_{24}$alkenyl, unsubstituted or $C_1$–$C_4$alkyl-substituted $C_5$–$C_{12}$cycloalkyl; unsubstituted or $C_1$–$C_4$alkyl-substituted $C_5$–$C_{12}$cycloalkenyl; or $C_7$–$C_9$phenylalkyl which is unsubstituted or substituted on the phenyl ring by $C_1$–$C_4$alkyl;

if n is 2, $R_6$ is $C_1$–$C_{25}$alkylene, $C_4$–$C_{25}$alkylene which is interrupted by oxygen, sulfur or

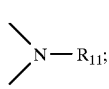

$C_4$–$C_{18}$alkenylene, phenylethylene,

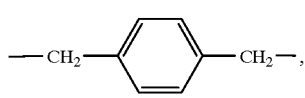

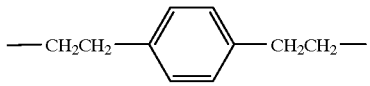

or $C_6$–$C_8$cycloalkylene; or $R_6$ furthermore is a radical of the formula III, IV or V

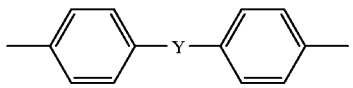

(III)

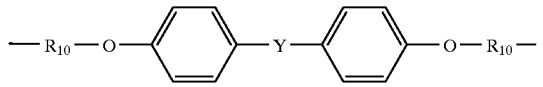

(IV)

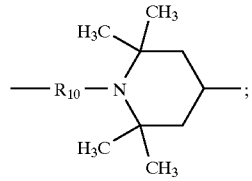

(V)

$R_7$ is $C_1$–$C_{18}$alkyl, unsubstituted or $C_1$–$C_4$alkyl-substituted $C_5$–$C_{12}$cycloalkyl; unsubstituted or $C_1$–$C_4$alkyl-substituted phenyl; $C_7$–$C_9$phenylalkyl or —(CH$_2$)$_r$COOR$_8$, $R_8$ is $C_1$–$C_{18}$alkyl, unsubstituted or $C_1$–$C_4$alkyl-substituted $C_5$–$C_{12}$cycloalkyl; unsubstituted or $C_1$–$C_4$alkyl-substituted phenyl; or $C_7$–$C_9$phenylalkyl;

$R_9$ is $C_1$–$C_{25}$alkyl, unsubstituted or $C_1$–$C_4$alkyl-substituted phenyl; $C_7$–$C_9$phenylalkyl, $C_1$–$C_{25}$alkanoyl, $C_3$–$C_{25}$alkenoyl, $C_2$–$C_{25}$alkanoyl which is interrupted by oxygen, sulfur or

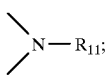

$C_6$–$C_9$cycloalkylcarbonyl, unsubstituted or $C_1$–$C_{12}$alkyl-substituted benzoyl; thienoyl or furoyl, $R_{10}$ is $C_1$–$C_{18}$alkylene, $C_4$–$C_{18}$alkylene which is interrupted by oxygen, sulfur or

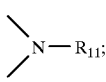

$C_4$–$C_8$alkenylene, phenylethylene,

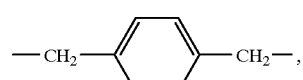

or

-continued

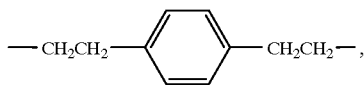

$R_{11}$ is hydrogen or $C_1$–$C_8$alkyl, $R_{12}$ and $R_{13}$, independently of one another, are hydrogen, $CF_3$, $C_1$–$C_{12}$alkyl or phenyl, or $R_{12}$ and $R_{13}$, together with the carbon atom to which they are bonded, form an unsubstituted or $C_1$–$C_4$alkyl-substituted $C_5$–$C_8$cycloalkylidene ring;

$R_{14}$ is hydrogen, $C_1$–$C_8$alkyl or a radical of the formula VI

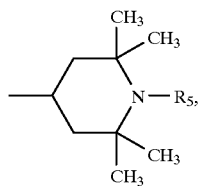 (VI)

X is oxygen or

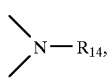

Y is a direct bond, oxygen, sulfur or

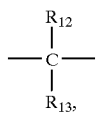

n is 1 or 2, p is 0, 1 or 2, q is an integer from 3 to 8, and r is 1 or 2.

2. A compound according to claim 1, in which $R_1$ and $R_2$, independently of one another, are hydrogen, $C_1$–$C_{18}$alkyl, $C_2$–$C_{18}$alkenyl, $C_5$–$C_8$cycloalkyl, unsubstituted or $C_1$–$C_4$alkyl-substituted phenyl; $C_5$–$C_8$cycloalkenyl, $C_7$–$C_9$phenylalkyl or —CH$_2$—S—R$_7$, $R_4$ is hydrogen, $C_1$–$C_{18}$alkyl, $C_2$–$C_{18}$alkenyl, $C_5$–$C_8$cycloalkyl, unsubstituted or $C_1$–$C_4$alkyl-substituted phenyl; $C_5$–$C_8$-cycloalkenyl, $C_7$–$C_9$-phenylalkyl, —CH$_2$—S—R$_7$, —(CH$_2$)$_p$COOR$_8$ or —(CH$_2$)$_q$OR$_9$, $R_5$ is hydrogen, $C_1$–$C_4$alkyl, OH, —CH$_2$CN, $C_4$–$C_{18}$alkoxy, $C_5$–$C_{12}$cycloalkoxy, allyl, propargyl, acetyl or $C_7$–$C_9$phenylalkyl; or $R_5$ furthermore is a radical of the formula II

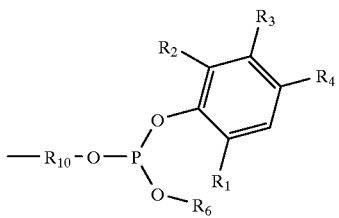 (II)

in which $R_6$ is as defined below for n=1, if n is 1, $R_6$ is $C_1$–$C_{18}$alkyl, $C_3$–$C_{18}$alkyl which is interrupted by oxygen, sulfur or

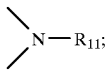

$C_2$–$C_{18}$alkenyl, $C_5$–$C_{12}$cycloalkyl, $C_5$–$C_{12}$cycloalkenyl or $C_7$–$C_9$phenylalkyl which is unsubstituted or substituted on the phenyl ring by $C_1$–$C_4$alkyl;

if n is 2, $R_6$ is $C_1$–$C_{18}$alkylene, $C_4$–$C_{18}$alkylene which is interrupted by oxygen, sulfur or

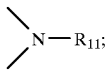

$C_4$–$C_{12}$alkenylene,

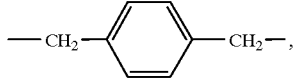

or $C_6$–$C_8$-cycloalkylene; or $R_6$ furthermore is a radical of the formula III or V

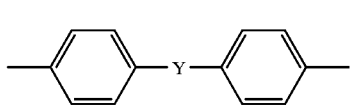 (III)

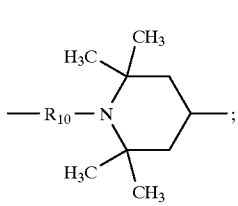 (V)

$R_7$ is $C_1$–$C_{18}$alkyl, $C_5$–$C_{12}$cycloalkyl, unsubstituted or $C_1$–$C_4$alkyl-substituted phenyl; $C_7$–$C_9$phenylalkyl or —(CH$_2$)$_r$COOR$_8$, $R_8$ is $C_1$–$C_{18}$alkyl, $C_5$–$C_{12}$cycloalkyl, unsubstituted or $C_1$–$C_4$alkyl-substituted phenyl; or $C_7$–$C_9$phenylalkyl, $R_9$ is $C_1$–$C_{18}$alkyl, unsubstituted or $C_1$–$C_4$alkyl-substituted phenyl; $C_7$–$C_9$phenylalkyl, $C_1$–$C_{18}$alkanoyl, $C_3$–$C_{18}$alkenoyl, $C_2$–$C_{18}$alkanoyl which is interrupted by oxygen, sulfur or

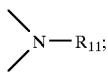

$C_6$–$C_9$cycloalkylcarbonyl, or unsubstituted or $C_1$–$C_4$alkyl-substituted benzoyl, $R_{10}$ is $C_1$–$C_{12}$alkylene, $C_4$–$C_{12}$alkylene which is interrupted by oxygen, sulfur or

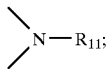

$C_4$–$C_8$alkenylene,

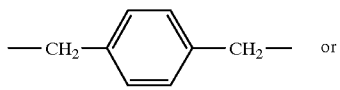 or

, $R_{12}$ and $R_{13}$, independently of one another, are hydrogen, $CF_3$, $C_1$–$C_8$alkyl or phenyl, or $R_{12}$ and $R_{13}$, together with the carbon atom to which they are bonded, form a $C_5$–$C_8$cycloalkylidene ring; and $R_{14}$ is hydrogen or $C_1$–$C_8$alkyl.

3. A compound according to claim 1, in which $R_1$, $R_2$ and $R_4$, independently of one another, are hydrogen, $C_1$–$C_8$alkyl, cyclohexyl or phenyl.

4. A compound according to claim 1, in which,
if n is 1,
$R_6$ is $C_1$–$C_{12}$alkyl, cyclohexyl or benzyl, and
if n is 2,
$R_6$ is $C_2$–$C_8$alkylene, $C_4$–$C_8$alkylene which is interrupted by

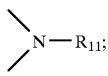

or a radical of the formula III or V

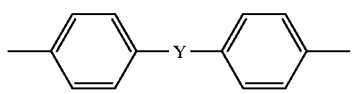

(III)

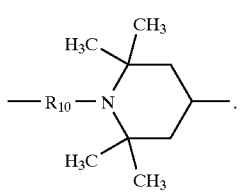

(V)

5. A compound according to claim 1, in which
$R_1$ and $R_2$, independently of one another, are hydrogen, $C_1$–$C_{12}$alkyl, $C_2$–$C_{12}$alkenyl, cyclohexyl, phenyl, cyclohexenyl or benzyl, $R_4$ is hydrogen, $C_1$–$C_{12}$alkyl, $C_2$–$C_{12}$alkenyl, cyclohexyl, phenyl, cyclohexenyl, benzyl, —$CH_2$—S—$R_7$, —$(CH_2)_p COOR_8$ or —$(CH_2)_q OR_9$, $R_5$ is hydrogen, $C_1$–$C_4$alkyl, $C_4$–$C_{16}$alkoxy, $C_5$–$C_8$cycloalkoxy, allyl, propargyl, acetyl or benzyl;

if n is 1, $R_6$ is $C_1$–$C_{12}$alkyl, $C_3$–$C_{12}$alkyl which is interrupted by oxygen or

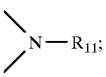

$C_2$–$C_{12}$-alkenyl, cyclohexyl, cyclohexenyl or benzyl;

if n is 2, $R_6$ is $C_1$–$C_{12}$alkylene, $C_4$–$C_{12}$alkylene which is interrupted by oxygen or

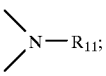

$C_4$–$C_8$-alkenylene or cyclohexylene; or $R_6$ furthermore is a radical of the formula III or V

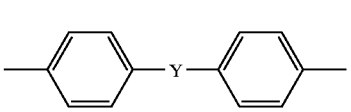

(III)

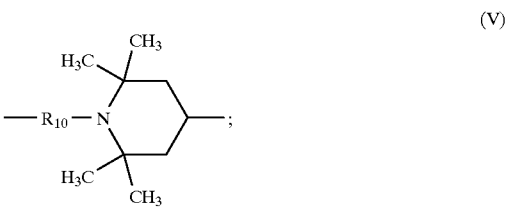

(V)

$R_7$ is $C_1$–$C_{12}$alkyl, $C_5$–$C_8$cycloalkyl, phenyl, benzyl or —$(CH_2)_r COOR_8$, $R_8$ is $C_1$–$C_{12}$alkyl, $C_5$–$C_8$cycloalkyl, phenyl or benzyl, $R_9$ is $C_1$–$C_{12}$alkyl, phenyl, benzyl, $C_1$–$C_{12}$alkanoyl, $C_2$–$C_{12}$alkanoyl which is interrupted by oxygen; cyclohexylcarbonyl or benzoyl, $R_{10}$ is $C_1$–$C_8$alkylene, $C_4$–$C_8$alkylene which is interrupted by oxygen; or $C_4$–$C_8$alkenylene, $R_{12}$ and $R_{13}$, independently of one another, are hydrogen, $CF_3$ or $C_1$–$C_4$alkyl, or $R_{12}$ and $R_{13}$, together with the carbon atom to which they are bonded, form a cyclohexylidene ring;

Y is a direct bond, oxygen or

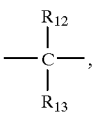

p is 2,
q is an integer from 3 to 6, and
r is 1.

6. A compound according to claim 1, in which
$R_1$ and $R_2$, independently of one another, are hydrogen, $C_1$–$C_8$alkyl, cyclohexyl or phenyl, $R_4$ is hydrogen, $C_1$–$C_8$alkyl, cyclohexyl or —$(CH_2)_p COOR_8$, $R_5$ is hydrogen, $C_1$–$C_4$alkyl, $C_6$–$C_{12}$alkoxy, acetyl or benzyl;

if n is 1, $R_6$ is $C_1$–$C_{12}$alkyl, cyclohexyl or benzyl;

if n is 2, $R_6$ is $C_2$–$C_8$alkylene, $C_4$–$C_8$alkylene which is interrupted by

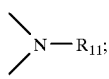

or a radical of the formula III or V

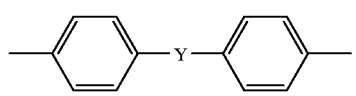

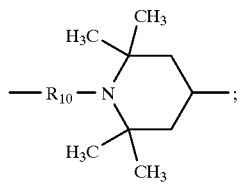

$R_8$ is $C_1$–$C_{12}$alkyl or benzyl, $R_{10}$ is $C_1$–$C_8$alkylene or $C_4$–$C_8$alkylene which is interrupted by oxygen, $R_{12}$ and $R_{13}$, independently of one another, are hydrogen or $C_1$–$C_4$alkyl, or $R_{12}$ and $R_{13}$, together with the carbon atom to which they are bonded, form a cyclohexylidene ring;

Y is a direct bond or

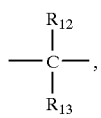

and p is 2.

7. A compound according to claim 1, in which $R_1$ and $R_2$, independently of one another, are $C_1$–$C_4$alkyl, $R_3$ is hydrogen, $R_4$ is $C_1$–$C_4$alkyl, $R_5$ is methyl;

if n is 1, $R_6$ is $C_1$–$C_{12}$alkyl or benzyl, if n is 2, $R_6$ is propylene, butylene which is interrupted by

or a radical of the formula V

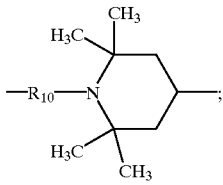

$R_{10}$ is ethylene, $R_{11}$ is methyl, $R_{14}$ is $C_1$–$C_4$alkyl,

X is oxygen or

\\
>N—$R_{14}$,
/ and n is 1 or 2.

8. A composition comprising
  a) an organic material which is subjected to oxidative, thermal or light-induced degradation and
  b) at least one compound of the formula I according to claim 1.

9. A composition according to claim 8, additionally comprising further additives in addition to components (a) and (b).

10. A composition according to claim 9, wherein the further additives are phenolic antioxidants, light stabilizers and/or processing stabilizers.

11. A composition according to claim 9, wherein the further additive is at least one compound of the benzofuran-2-one type.

12. A composition according to claim 8, wherein component (a) is a natural, semisynthetic or synthetic polymer.

13. A composition according to claim 8, wherein component (a) is a thermoplastic polymer.

14. A composition according to claim 8, wherein component (a) is a polyolefin.

15. A composition according to claim 8, wherein component (a) is polyethylene or polypropylene.

16. A process for the stabilization of an organic material against oxidative, thermal or light-induced degradation, which comprises incorporating or applying at least one compound of the formula I defined in claim 1 into or to this material.

* * * * *